United States Patent [19]

Moriuchi et al.

[11] Patent Number: 5,076,280
[45] Date of Patent: Dec. 31, 1991

[54] DEVICE FOR CORRECTING BLOOD PRESSURE WAVEFORM

[75] Inventors: Yousuke Moriuchi; Fumihisa Hirose, both of Fuji, Japan

[73] Assignee: Terumo Kabushiki Kaisha, Tokyo, Japan

[21] Appl. No.: 307,938

[22] Filed: Feb. 9, 1989

[30] Foreign Application Priority Data

Feb. 12, 1988 [JP] Japan .................................. 63-30164

[51] Int. Cl.$^5$ .............................................. A61B 5/02
[52] U.S. Cl. ...................................... 128/672; 73/707; 73/756; 128/748
[58] Field of Search ........................ 128/672–673, 128/675, 674, 748; 73/707, 756; 137/269; 251/118

[56] References Cited

U.S. PATENT DOCUMENTS

| | | |
|---|---|---|
| 3,610,228 | 10/1971 | Temkin . |
| 3,865,100 | 2/1975 | Kanai et al. ........................ 128/675 |
| 3,901,402 | 8/1975 | Ayres ................................. 128/764 X |
| 4,335,729 | 6/1982 | Reynolds et al. . |
| 4,431,009 | 2/1984 | Marino et al. . |
| 4,517,844 | 5/1985 | Powell ............................... 128/672 |
| 4,779,625 | 10/1988 | Cole ................................... 128/748 X |
| 4,795,440 | 1/1989 | Young et al. ...................... 128/675 X |

Primary Examiner—Lee S. Cohen
Assistant Examiner—John P. Lacyk
Attorney, Agent, or Firm—Burns, Doane, Swecker & Mathis

[57] ABSTRACT

The waveform of a blood pressure of a patient is corrected by a pressure correcting mechanism having an air chamber having a volume ranging from 1 to 150 μl and a resistance passage having one end communicating with the air chamber and the other end with a blood pressure measuring line. The resistance passage has a cross-sectional area ranging from 2000 to 160,000 μm$^2$ and a length ranging from 0.5 to 40 mm. A fluid such as a physiological saline solution filled in the blood pressure measuring line can flow through the resistance passage into the air chamber to dampen an extraneous pressure wave transmitted through the blood pressure measuring line.

14 Claims, 5 Drawing Sheets

DEVICE FOR CORRECTING BLOOD PRESSURE WAVEFORM

BACKGROUND OF THE INVENTION

The present invention relates to a blood pressure waveform correcting device for producing an accurate blood pressure waveform in a blood monitoring system.

Blood pressure monitoring systems are employed in the medical field for monitoring, at all times, the blood pressure of a patient which varies from time to time. Such blood pressure monitoring systems as well as systems for controlling anesthesia are relied upon in surgical operations, for example.

In a blood pressure monitoring system, a catheter placed in a blood vessel of a patient is connected to a pressure transducer through a blood pressure measuring line including a pressure transmitting tube and a pressure dome, and the pressure transducer is coupled to a CRT display unit or a recorder unit.

The catheter placed at a point for measuring the blood pressure of the patient and the blood pressure measuring line are filled with a physiological saline solution for the following reasons:

If air were left trapped in the catheter or the blood pressure measuring line, since air which is highly compressible is of large compliance, it would obstruct proper blood pressure transmission and also vary frequency characteristics of the blood pressure. To avoid this problem, priming is performed to remove air from the catheter and the blood pressure measuring line before the catheter is inserted into a blood vessel.

To effect priming, a physiological saline solution is injected via one port of a three-way cock in the pressure transmitting tube until the physiological saline solution overflows the catheter and an outlet port of the pressure dome. The physiological saline solution thus filled in the catheter and the blood pressure measuring line is used as a pressure transmitting medium. The blood pressure which is transmitted via the physiological saline solution is applied to a diaphragm in the pressure dome, and the applied pressure is converted to an electric signal by the pressure transducer. The blood pressure signal can directly be monitored or displayed on the CRT display unit or recorded on the recorder unit.

To allow for easy handling in a measuring process, the pressure transmitting tube comprises a flexible tube such as a soft tube of vinyl chloride or the like. Since the tube wall of the pressure transmitting tube pulsates in resonance with the pulsation of the patient's heart, the physiological saline solution in the pressure transmitting tube is subjected to an additional pressure developed by the throbbing tube wall as well as the blood pressure of the patient. This extraneous throbbing pressure is also transmitted to the diaphragm in the pressure dome, and will be observed as a distorted blood pressure waveform on the CRT display unit.

More specifically, since the pressure transmitting tube filled up with the physiological saline solution is present between the catheter and the pressure transducer, the blood pressure monitoring system has its own damping factor D and resonance frequency f due to the physical properties of the catheter, the pressure transmitting tube, and the pressure transducer. The blood pressure monitoring system is normally underdamped with the damping factor D ranging from 0.2 to 0.3. Because the damping factor D and the resonance frequency f are not of appropriate values, the blood pressure waveform as measured by the pressure transducer is distorted as compared with a desired blood pressure waveform. The resonance of the system is of a frequency which is several times higher than the frequency of the blood pressure, and has small vibration energy.

The damping factor D is defined as:

$$D = \sqrt{\frac{(\ln(X_2/X_1))^2}{\pi^2 + \ln(X_2/X_1)}} \quad (1)$$

where $X_1$, $X_2$ are the amplitudes shown in FIG. 1 of the accompanying drawings. The resonance frequency f is expressed by $f = 1/t$ where t is the time (sec.) of one cycle shown in FIG. 1.

The damping factor D can be obtained by applying a pressure of 300 mmHg, for example, to the blood pressure measuring line, abruptly opening the three-way plug in the blood pressure measuring line, measuring the amplitudes $X_1$, $X_2$ of a waveform displayed on the CRT display unit, and putting the measured values $X_1$, $X_2$ in the above equation (1). If the damping factor D and the resonance frequency f are not appropriately related to each other, no accurate blood pressure waveform can be measured. A range in which the damping factor D and the resonance frequency f are of suitable relationship and an accurate blood pressure waveform can be measured varies with the pulse rate of the patient. As shown in FIG. 2, such a range for a patient having a pulse rate of 60 is on the righthand side of the curve E, and such a range for a patient having a pulse rate of 120 is on the righthand side of the curve F, the curves E, F being produced clinically. The best range for the damping factor D is from 0.4 to 0.6, including areas $E_T$, $F_T$ on the curves E, Various means for removing the effect of the resonance on the blood pressure measurement have been proposed (1) In order to prevent a fluid from moving due to resonant vibrations, a variable resistance means is inserted in series in the blood pressure measuring line (2) A membrane having a suitable degree of compliance is incorporated in the blood pressure measuring line to increase a damping factor due to the resiliency of the membrane.

(3) A variable resistance means and an air chamber are placed in the blood pressure measuring line.

With the proposal (1) above, however, the variable resistance means can be inserted only in a limited position in the blood pressure measuring line. More specifically, since the variable resistance means is placed in series in the blood pressure measuring line, if the variable resistance means were inserted in a wrong position, then the resistance means would make it impossible to flush the blood pressure measuring line. More specifically, the blood pressure measuring line is filled with a pressure transmitting line such as physiological saline solution. The physiological saline solution is forced to flow in a small amount into the patient's blood vessel in order to prevent the blood from flowing into and being solidified in the blood pressure line. In addition, a device is disposed in the blood pressure measuring line for flushing the line to remove foreign matter and blood from the line. Where the variable resistance means is inserted in the blood pressure measuring line according to the proposal (1), if a solution container for supplying the physiological saline solution, the variable resistance means, and the flushing device are arranged in this order, a desired amount of the flushing solution cannot flow downstream in the line because the resistance means is disposed upstream of the flushing device. When setting the variable resistance means in place, the resistance of the variable resistance means is progressively increased while looking at the CRT display unit to observe the manner in which the effect of the resonance is eliminated. Thus, delicate adjustments are required to determine a position to set the variable resistance means, The arrangement (2) above is effective in increasing the damping factor D due to the resiliency of the membrane, but reduces the resonance frequency f of the blood pressure measuring line, so that it will be difficult to measure accurate blood pressure waveforms.

According to the system (3) above, delicate adjustments are also required to establish a flow passage through the variable resistance means to the air chamber when setting the variable resistance means and the air chamber in place, and such delicate adjustments are time-consuming.

SUMMARY OF THE INVENTION

It is a major object of the present invention to provide a blood pressure waveform correcting device which can be incorporated in a blood pressure measuring line without limiting its position, does not lower the resonance frequency f of the blood pressure measuring line, does not require delicate adjustments when set up, and can produce accurate blood pressure waveforms.

Another object of the present invention is to provide a blood pressure waveform correcting device comprising a pressure correcting mechanism having an air chamber having a volume ranging from 1 to 150 $\mu$l and a resistance passage having one end communicating with said air chamber and the other end with a blood pressure measuring line, said resistance passage having a cross-sectional area ranging from 2000 to 160,000 $\mu m^2$ and a length ranging from 0.5 to 40 mm, whereby a fluid in the blood pressure measuring line can flow through said resistance passage into said air chamber to dampen an extraneous pressure wave transmitted through the blood pressure measuring line.

Still another object of the present invention is to provide a blood pressure waveform correcting device wherein said resistance passage comprises a straight passage, a curved passage, a passage composed of straight passages combined with each other, or a passage composed of straight and curved passages combined with each other.

Yet another object of the present invention is to provide a blood pressure waveform correcting device wherein said pressure correcting mechanism comprises a damping body defining said air chamber and said resistance passage therein, and a wall member held in intimate contact with said damping body to isolate said air chamber from outside of said damping body, said wall member being penetratable by a syringe needle.

Yet still another object of the present invention is to provide a blood pressure waveform correcting device wherein said wall member is made of a material capable of closing, of its own accord, a hole which has been pierced by the syringe needle.

A further object of the present invention is to provide a blood pressure waveform correcting device wherein said pressure correcting mechanism comprises a damping body defining said air chamber and said resistance passage therein, and a plug held in slidable contact with said damping body in a liquid-tight manner to isolate said air chamber from outside of said damping body and vary the volume of said air chamber.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
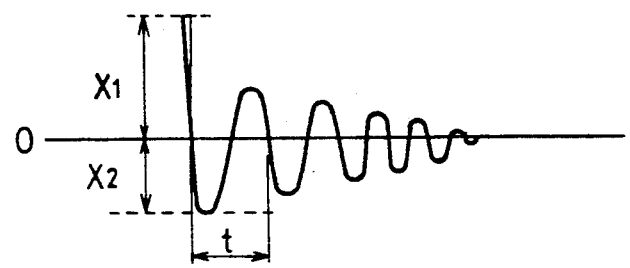
FIG. 1 is a diagram used to explain a damping factor.
Figure 2:
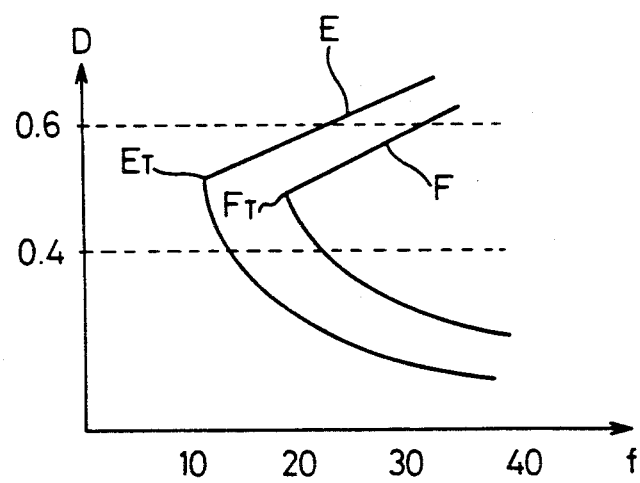
FIG. 2 is a graph showing the relationship between the damping factor and the resonance frequency.
Figure 3:
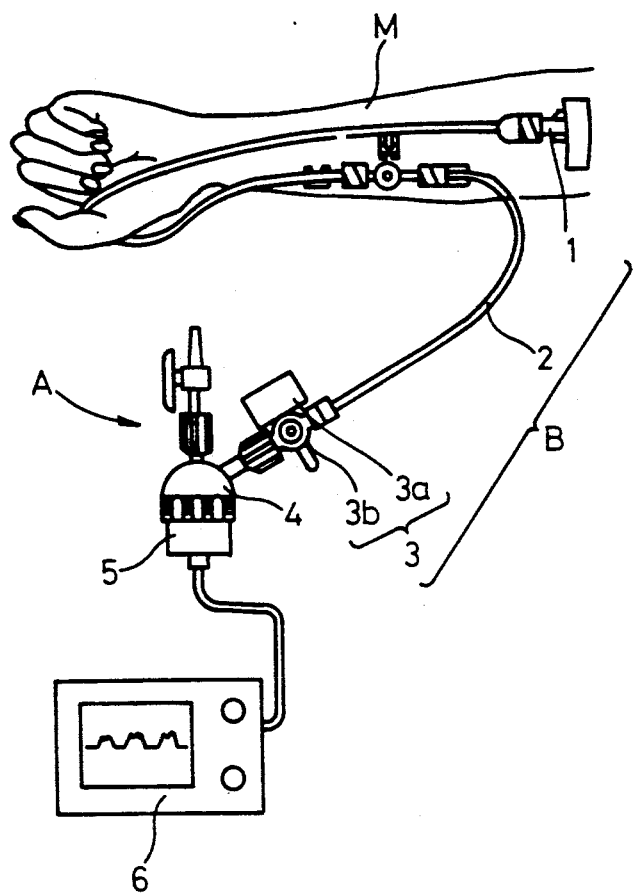
FIG. 3 is a schematic view of a blood monitoring system incorporating a blood pressure waveform correcting device according to the present invention.

As shown in FIG. 3, a blood monitoring system A includes a catheter 1 placed in a blood vessel of a patient M, a flexible pressure transmitting tube 2 connected to the catheter 1, a blood pressure waveform correcting device (hereinafter also referred to as a "correcting device") 3 having a three-way cock and connected to the pressure transmitting tube 2, and a pressure dome 4 connected to the correcting device 3. The pressure transmitting tube 2, the correcting device 3, and the pressure dome 4 jointly constitute a blood pressure measuring line B. The pressure dome 4 is connected to a pressure transducer 5 which is electrically connected to a CRT display unit 6 and a recorder unit (not shown). The blood pressure measuring line B is filled up with a pressure transmitting medium which may be a physiological saline solution C (described later on), for example, which will transmit the blood pressure of the patient M to a diaphragm in the pressure dome 4. The pressure applied to the diaphragm is converted to an electric signal by the pressure transducer 5 to enable the CRT display unit 6 and the recorder unit to directly display or monitor and record the blood pressure of the patient.

Figure 4:
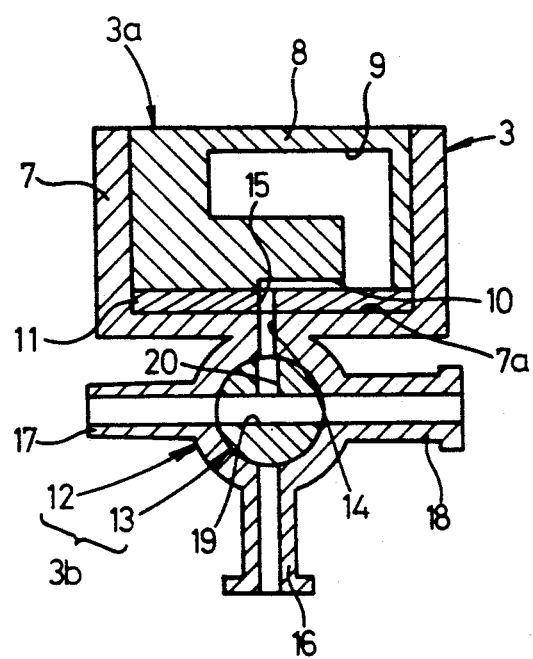
FIG. 4 is a cross-sectional view of the blood pressure waveform correcting device shown in FIG. 3.
Figure 5:
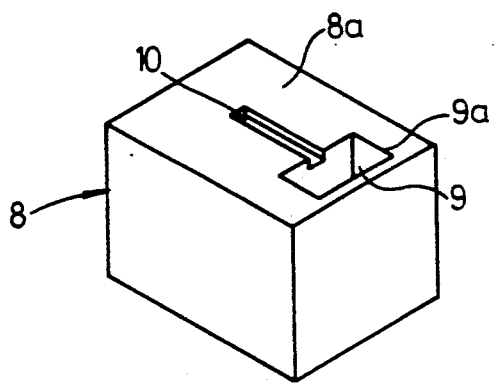
FIG. 5 is a perspective view of a damping body of the blood pressure waveform correcting device shown in FIG. 4.

In FIG. 4, the correcting device 3 incorporated in the blood pressure measuring line B of the system A comprises a correcting unit 3a serving as a pressure correcting mechanism and a three-way cock 3b. The correcting unit 3a comprises a housing 7, a damping body 8 disposed in the housing 7 in a liquid-tight manner and defining an air chamber 9 therein and a resistance passage 10 in a side surface 8a (see FIG. 5) thereof, and a packing 11 interposed between the side surface 8a and a bottom plate 7a of the housing 7. The three-way cock 3b comprises a valve casing 12 integrally formed with the housing 7, and a valve member 13 housed in the valve casing 12.

The housing 7 which is integral with the valve casing 12 is in the form of a box made of polycarbonate, for example. The box-shaped housing 7 further includes a communication passage 14 defined centrally through the bottom plate 7a and extending into the valve casing 12.

The damping body 8 is in the form of a rectangular parallelepiped and is also made of polycarbonate, for example. The air chamber 9 defined in the damping body 8 has an opening 9a (FIG. 5) defined in a side thereof, and is of a substantially L-shaped cross section. The air chamber 9 has a volume which ranges from 1 to 150 $\mu$l, preferably from 5 to 80 $\mu$l, and more preferably from 10 to 60 $\mu$l. If the volume of the air chamber 9 were smaller than 1 $\mu$l or larger than 150 $\mu$l, then it may not provide an appropriate damping factor D and an appropriate resonance frequency f, and accurate blood pressure waveforms may not be produced. In the embodiment of FIG. 4, the volume of the air chamber 9 is of 40 $\mu$l.

The resistance passage 10 in the form of a groove is defined in the side surface 8a of the damping body 8. The resistance passage 10 has one end communicating with the opening 9a of the air chamber 9, and the other end with the communication passage 14 in the housing 7 and the valve casing 12 through a hole 15 defined in the packing 11. The resistance passage 10 has a cross-sectional area (FIG. 4) which ranges from 2000 to 160,000 $\mu m^2$, preferably from 5000 to 100,000 $\mu m^2$, and more preferably from 15,000 to 70,000 $\mu m^2$. If the cross-sectional area of the resistance passage 10 were smaller than 2000 $\mu m^2$ or larger than 160,000 $\mu m^2$, then then it may not provide an appropriate damping factor D and an appropriate resonance frequency f, and accurate blood pressure waveforms may not be produced. The resistance passage 10 has a length which ranges from 0.5 to 40 mm, preferably from 1 to 30 mm, and more preferably from 3 to 20 mm. If the length of the resistance passage 10 were smaller than 0.5 mm or larger than 40 mm, then it may not provide an appropriate damping factor D and an appropriate resonance frequency f, and accurate blood pressure waveforms may not be produced. If the resistance passage 10 were shorter than 0.5 mm, air might be trapped into the blood pressure measuring line B. The illustrated resistance passage 10 is shaped as a channel groove and has a width of 0.2 mm, a length of 4.0 mm, and a depth of 0.17 mm. The volume of the air chamber 9, the cross-sectional area of the resistance passage 10, and the length of the resistance passage 10 are related such that when the resistance imposed by the resistance passage 10 is large, i.e., when the length of the resistance passage 10 is large and the cross-sectional area thereof is small, an appropriate damping factor D can be obtained by reducing the volume of the air chamber 9. The cross-sectional area of the resistance passage 10 is sufficiently smaller than the cross-sectional area of the pressure transmitting tube 2 of the blood pressure measuring line B.

Figure 6:
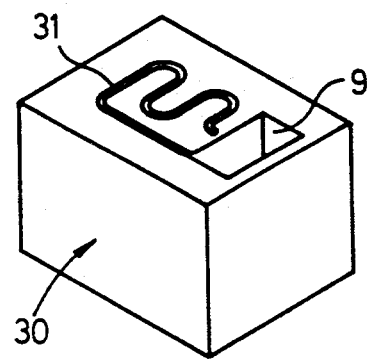
FIG. 6 is a perspective view of a damping body according to another embodiment.

FIG. 6 shows a damping body according to another embodiment of the present invention. The damping body, generally denoted at 30, has a resistance passage 31 made up of a combination of straight and curved passage segments. The other details of the damping body of FIG. 6 are the same as those of the damping body shown in FIG. 5, and are denoted by identical reference numerals.

The resistance passage 31 defined in the damping body 30 has an increased length for applying a large resistance to a physiological saline solution C flowing through the resistance passage 31 to reduce the speed of travel of the solution C through the resistance passage 31. Therefore, even when a negative pressure is developed in the blood pressure measuring line B, no air is introduced from the air chamber 9 into the blood pressure measuring line B. The same advantage can be obtained by defining a resistance passage of a tortuous shape, a W shape, a C shape, or a shape of a combination of these shapes, in a damping body.

Referring back to FIG. 4, the packing 11 is made up of silicone rubber, and is interposed intimately between the bottom plate 7a of the housing 7 and the side surface 8a of the damping body 8 to prevent air and the physiological saline solution C from leaking out of the air chamber 9 and the resistance passage 10. The valve casing 12 is hollow and substantially cylindrical in shape and has a fluid port 16 in coaxial relation to the communication passage 14. The fluid port 16 is connected to a fluid supply set (not shown). The valve casing 12 also has a tube port 17 and a dome port 18 which are defined therein and extend away from each other in directions normal to the communication passage 14. The tube port 17 and the dome port 18 are coupled respectively to the pressure transmitting tube 2 and the pressure dome 4.

Figure 7:
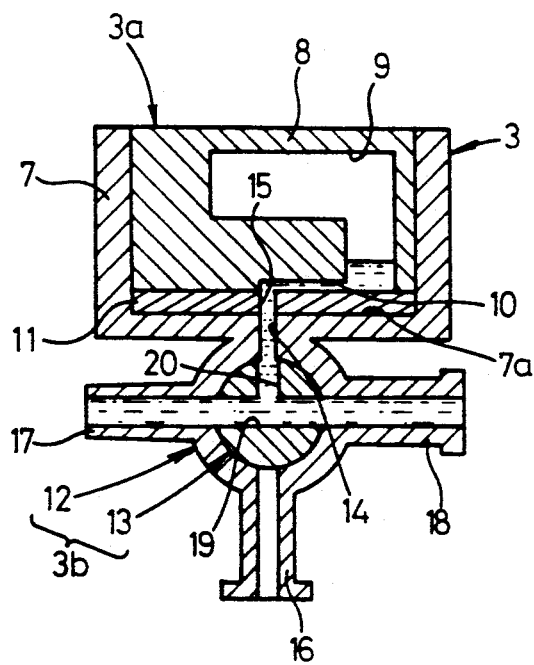
FIG. 7 is a cross-sectional view of the blood pressure waveform correcting device of FIG. 4 at the time of measuring a blood pressure.
Figure 8:
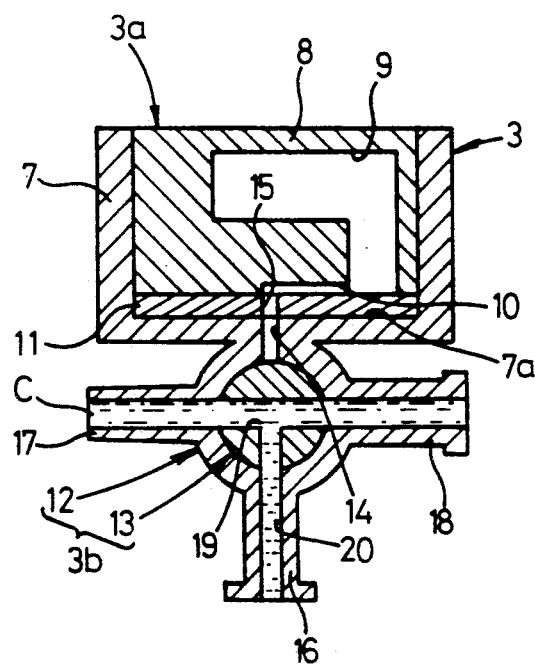
FIG. 8 is a cross-sectional view of the blood pressure waveform correcting device of FIG. 4 at the time of priming.

The valve member 13 is also of a substantially cylindrical shape and angularly movably disposed in the hollow cylinder of the valve casing 12 in a liquid-tight manner. The valve member 13 has a passage 19 defined therein and extending diametrically therethrough, and a passage 20 defined therein radially and communicating perpendicularly with the passage 19. When measuring a blood pressure, the passage 20 is connected to the passage 14, and the passage 19 is connected to the tube port 19 and the dome port 18, as shown in FIG. 7. For priming the system A, the passage 20 is connected to the fluid port 16, and the passage 19 is connected to the tube port 17 and the dome port 18, as illustrated in FIG. 8.

Operation of the blood monitoring system A incorporating the blood pressure waveform correcting device 3 of the above structure will be described below.

The tube port 17 of the three-way cock 3b is coupled to the catheter 1 through the pressure transmitting tube 2, and the pressure dome 4 is coupled to the dome port 18 of the three-way cock 3b, thus completing the blood pressure line B. The pressure transducer 5 is then connected to the pressure dome 4, and the CRT display unit 6 and, if necessary, the recorder unit are hooked up, thus setting up the system A.

Then, the fluid supply set (not shown) filled with a physiological saline solution is connected to the fluid port 16 of the three-way cock 3b. The valve member 13 is then turned to connect the passage 20 to the fluid port 16 and the passage 19 to the tube port 17 and the dome port 18 to introduce the physiological saline solution C into the blood pressure measuring line B. Then, the system A is primed by causing the physiological saline solution to overflow the outlet ports of the catheter 1 and the pressure dome 4, thus removing air from the blood pressure measuring line B. The valve member 13 is turned again to connect the passage 20 to the communication passage 14 and the passage 19 to the tube port 17 and the dome port 18.

The catheter 1 is inserted into a blood vessel of a patient M to start a blood pressure measuring process. At that time, a positive pressure is developed in the blood pressure measuring line B since the blood pressure is applied thereto. Therefore, the physiological saline solution C flows into the air chamber 9 via the passage 20, the communication passage 14, the hole 15, and the resistance passage 10. A pressure wave which travels toward the diaphragm in the pressure dome 4 through the intermediary of the physiological saline solution C reaches the air chamber 9 via the passage 20, the communication passage 14, the hole 15, and the resistance passage 10, and is dampened by the compliance of air in the air chamber 9. As a result, the damping factor D of the entire blood pressure measuring line B is increased. Even if the pressure transmitting tube 2 resonates while measuring the blood pressure, such resonance is not detected by the diaphragm in the pressure dome 4, but only the blood pressure of the patient M is converted to an electric signal by the pressure transducer 5. Therefore, a normal blood pressure waveform is displayed on the CRT display unit 6, and may also be recorded on the recorder unit if desired.

An experiment was conducted to see if the damping factor D and the resonance frequency f vary dependent on the length of the pressure transmitting tube 2 of the blood pressure measuring line B. The results of such an experiment will be described below.

A 20 G indwelling needle was used as the catheter 1. Pressure transmitting tubes 2 of different lengths of 120 cm, 90 cm, 60 cm, 30 cm (the length of the tube 2 extends from the indwelling needle to the correcting device 3, excluding the length of the three-way cock 3b or any other solid member disposed in the tube 2) were successively incorporated in the blood pressure measuring line B, and damping factors D and resonance frequencies f obtained when these pressure transmitting tubes 2 of the different lengths were measured (see Table 1). As a comparison, damping factors D and resonance frequencies f when no correcting device 3 was combined with the blood pressure measuring line B were also measured (see Table 2).

TABLE 1

| Catheter | Pressure transmitting tube | Damping factor | Resonance frequency |
|---|---|---|---|
| 20G* | 120 cm long | 0.57 | 25 Hz |
| " | 90 cm long | 0.57 | 32.1 Hz |
| " | 60 cm long | 0.58 | 35.7 Hz |
| " | 30 cm long | 0.56 | 41.7 Hz |
| Avg. | — | 0.57 | — |

*Indwelling needle

TABLE 2

| Catheter | Pressure transmitting tube | Damping factor | Resonance frequency |
|---|---|---|---|
| 20G* | 120 cm long | 0.16 | 25 Hz |
| " | 90 cm long | 0.17 | 31.2 Hz |
| " | 60 cm long | 0.18 | 35.7 Hz |
| " | 30 cm long | 0.19 | 41.7 Hz |
| Avg. | — | 0.175 | — |

Indwelling needle

The results given in the Tables 1 and 2 indicate that the damping factor D provided by the correcting device 3 of the invention is not varied dependent on the position where the correcting device 3 is located in the blood pressure measuring line B, but remains substantially constant in the range of from 0.5 to 0.6, and that the damping factor D of the invention is higher than the damping factor (ranging from 0.16 to 0.19) of the comparative example by 0.3 to 0.4. The resonance frequency f is not lowered unlike the resonance frequency of the prior art systems. Consequently, the blood pressure waveform displayed on the CRT display unit 6 is highly normal and free of distortions independently of the pressure transmitting tube 2.

Figure 9:
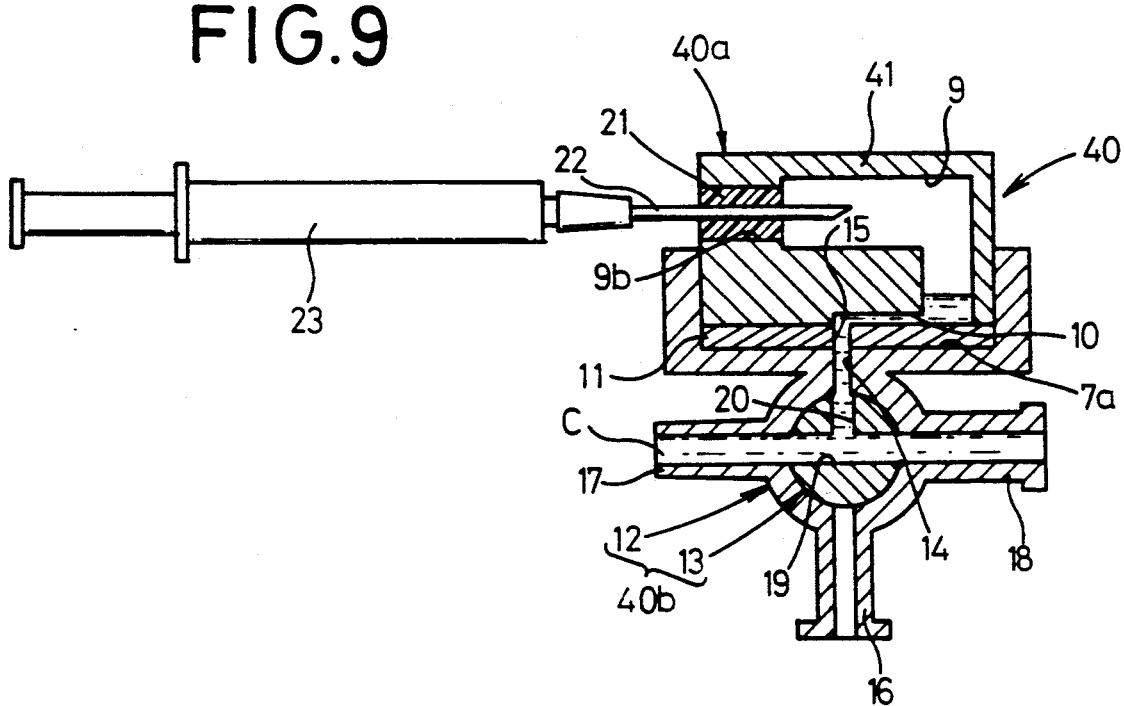
FIGS. 9 and 10 are cross-sectional views of a blood pressure waveform correcting device according to another embodiment of the present invention.
Figure 10:
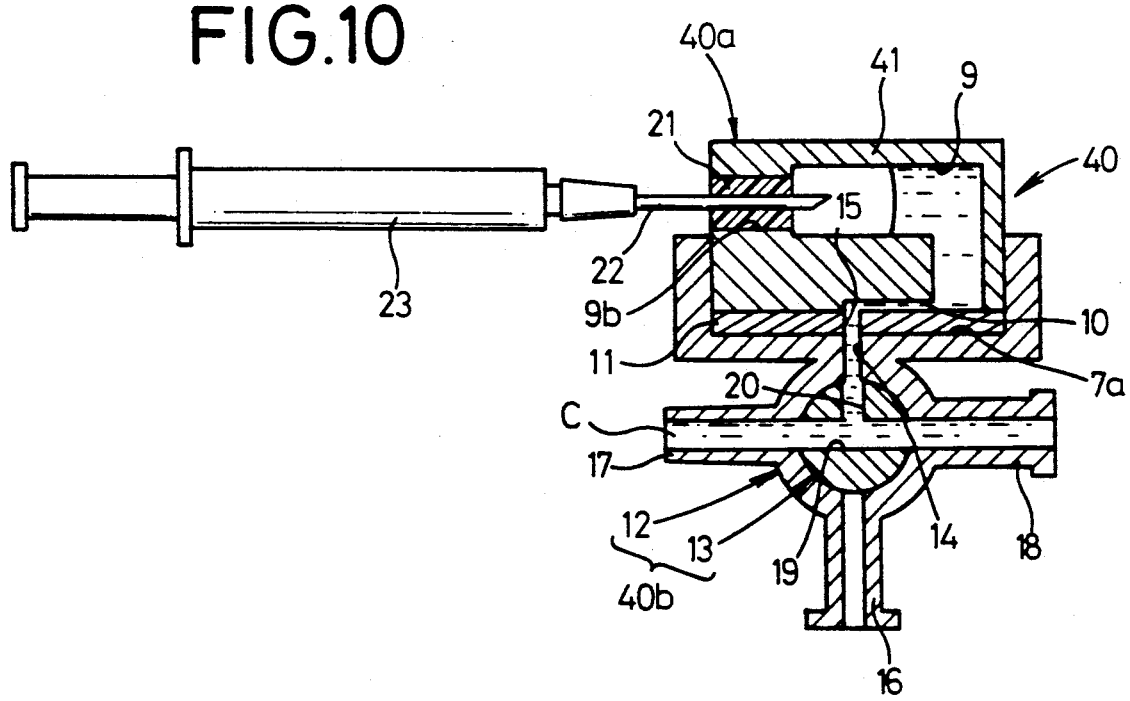

FIGS. 9 and 10 illustrate a blood pressure waveform correcting device in accordance with another embodiment of the present invention. The blood pressure waveform correcting device, denoted at 40, comprises a correcting unit 40a and a three-way cock 40b integrally formed with the correcting unit 40a. Those components of the correcting device 40 which are identical to those of the correcting device 3 shown in FIG. 4 are denoted by identical reference numerals.

The correcting unit 40a includes a damping body 41 defining an air chamber 9 therein and having a hole 9b defined in a wall of the air chamber 9. A thick wall member 21 made of silicone rubber is fitted in the hole 9b. The wall member 21 of silicone rubber allows the needle 22 of a syringe 23 to penetrate the same with ease, and also permits the pierced hole to be closed of its own accord under the resiliency of silicone rubber after the syringe needle 22 has been pulled out.

The correcting device 40 is effective in preventing air in the air chamber 9 from being forced into the blood pressure measuring line B even when a negative pressure is developed in the line B. More specifically, when the blood monitoring system is primed with a physiological saline solution C, the needle 22 of the syringe 23 having a small volume is forced through the silicone rubber wall member 21. Then, after either a suitable amount of air is removed by the syringe 23 from the air chamber 9 until an amount of air ranging from 40 to 50 μl is left in the air chamber 9 where the volume of the air chamber 9 is of 100 μl (see FIG. 9), or air is fully removed from the air chamber 9 by the syringe 23, a suitable amount of air is introduced again into the air chamber 9 (see FIG. 10). In this manner, even if the blood pressure measuring line B is of a negative pressure, 60 to 50 μl (=100−(40 to 50)) or 100 μl of the physiological saline solution C can be fed into the blood pressure measuring line B.

Figure 11:
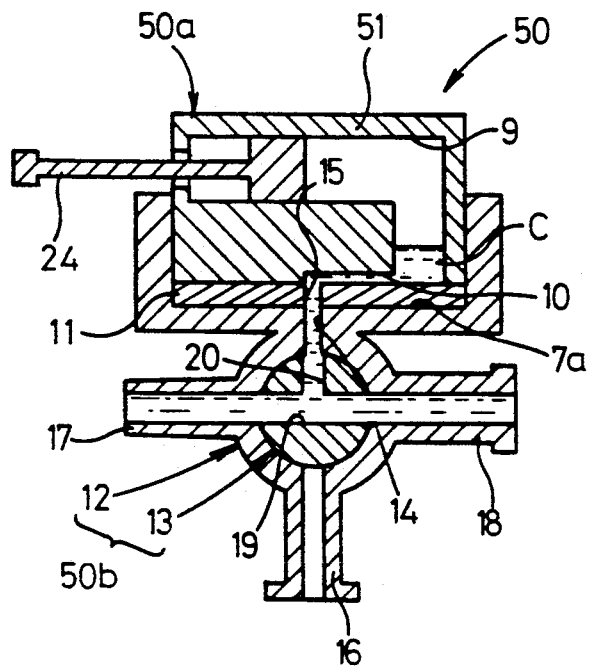
FIGS. 11 and 12 are cross-sectional views of a blood pressure waveform correcting device according to still another embodiment of the present invention.
Figure 12:
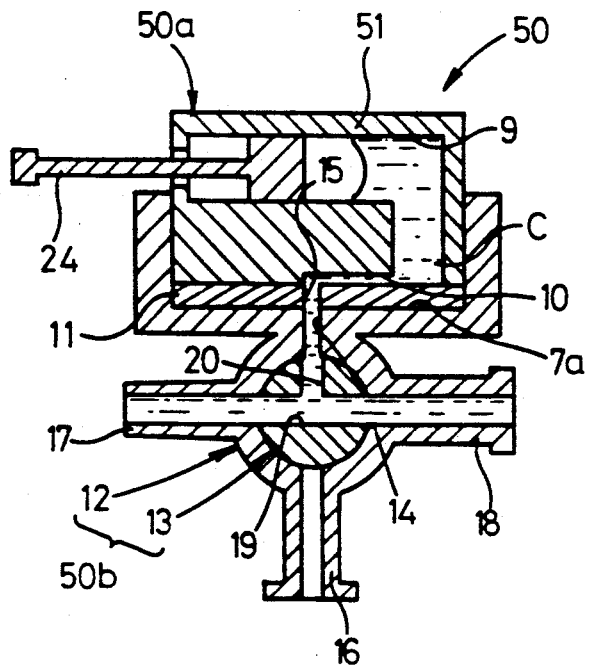

FIGS. 11 and 12 shows a blood pressure waveform correcting device according to still another embodiment of the present invention. The blood pressure waveform correcting device, denoted at 50, comprises a correcting unit 50a and a three-way cock 50b integrally formed with the correcting unit 50a. Those components of the correcting device 40 which are identical to those of the correcting device 3 shown in FIG. 4 are denoted by identical reference numerals.

The correcting unit 50a includes a damping body 51 defining an air chamber 9 therein. A plug 24 of silicone rubber is slidably disposed between a wall of the air chamber 9 and a side surface of the damping body 51 in a liquid-tight manner. The correcting device 50 prevents air from being introduced from the air chamber 9 into the blood pressure measuring line B even if a negative pressure is developed in the blood pressure measuring line B, as with the preceding embodiment of FIGS. 9 and 10.

With the present invention, as described above, a blood pressure waveform correcting device comprises a pressure correcting mechanism having an air chamber having a volume ranging from 1 to 150 µl and a resistance passage having one end communicating with the air chamber and the other end with a blood pressure measuring line, the resistance passage having a cross-sectional area ranging from 2000 to 160,000 µm$^2$ and a length ranging from 0.5 to 40 mm. Since the air chamber communicates with the blood pressure measuring line via the resistance passage, part of a fluid in the blood pressure measuring line to which a blood pressure is applied flows through the resistance passage into the air chamber. Therefore, a pressure wave which travels as a pressure transmitting medium through the blood pressure measuring line reaches the air chamber through the resistance passage, and is dampened by the compliance of air in the air chamber. As a consequence, the damping factor of the entire blood pressure measuring line is adjusted to an appropriate value, and the resonance frequency of the blood pressure measuring line is not lowered. The blood monitoring system can therefore produce accurate blood pressure waveforms.

Inasmuch as the position of the pressure correcting mechanism in the blood pressure measuring line is not limited, i.e., may be anywhere in the blood pressure measuring line, it is not necessary to effect delicate adjustments for setting up the correcting device while looking at the CRT display unit as with the conventional system.

Although certain preferred embodiments have been shown and described, it should be understood that many changes and modifications may be made therein without departing from the scope of the appended claims.

What is claimed is:

1. A blood pressure waveform correcting device, comprising:
   a pressure correcting mechanism having an air chamber and
   a resistance passage, one end of said resistance passage communicating with said air chamber and an opposite end communicating with a blood pressure measuring line, said resistance passage comprising a curved passage, a passage composed of straight passages connected to one another, or a passage composed of straight and curved passages connected to one another, and said pressure correcting mechanism being defined by a body positioned in a housing, said air chamber and said resistance passage being formed as a part of said body, said air chamber being airtight, and including a wall member held in intimate contact with said body to isolate said air chamber from outside of said body, said wall member being capable of being penetrated by a syringe needle whereby a fluid in the blood pressure measuring line can flow through said resistance passage into said airtight chamber to directly dampen an extraneous pressure wave transmitted through the blood pressure measuring line.

2. A blood pressure waveform correcting device according to claim 1, wherein said wall member is made of a material capable of closing, of its own accord, a hole which has been pierced by the syringe needle.

3. A blood pressure waveform correcting device according to claim 1, including a plug held in slidable contact with said body in a liquid-tight manner to isolate said air chamber from outside of said body and vary the volume of said air chamber.

4. The blood pressure waveform correcting device according to claim 1, wherein said airtight chamber has a volume ranging from about 1 µl to about 150 µl and said resistance passage has a cross-sectional area ranging from about 2000 µm$^2$ to about 160,000 µm$^2$ and a length ranging from about 0.5 mm to about 40 mm.

5. A blood pressure waveform correcting device comprising: a pressure correcting mechanism having an air chamber and a resistance passage that are formed as a part of a one-piece damping body, said air chamber having an opening that opens to one side of the damping body and said resistance passage also opening to said one side of the damping body, said air chamber being completely enclosed by said one-piece damping body except for the opening and said one side of said damping body being in intimate contact with a wall member which has a hole passing therethrough, said hole in the wall member communicating with a blood pressure measuring line, one end of said resistance passage communicating with said hole in the wall member and the other end of said resistance passage communicating with said opening in the air chamber, said wall member including means for permitting the wall member to be penetrated by a syringe needle whereby a fluid in the blood pressure measuring line can flow through said hole in the wall member, through the resistance passage and into the air chamber to dampen an extraneous pressure wave transmitted through the blood pressure measuring line.

6. A blood pressure waveform correcting device according to claim 5, wherein said resistance passage comprises a straight passage, a curved passage, a passage composed of straight passages combined with each other, or a passage composed of straight and curved passages combined with each other.

7. The blood pressure waveform correcting device according to claim 5, wherein said airtight chamber has a volume ranging from about 1 µl to about 150 µl and said resistance passage has a cross-sectional area ranging from about 2000 µm$^2$ to about 160,000 µm$^2$ and a length ranging from about 0.5 mm to about 40 mm.

8. The blood pressure waveform correcting device according to claim 5, wherein at least a portion of said wall member is made of a material capable of closing, of its own accord, a hole which has been pierced by a syringe needle.

9. The blood pressure waveform correcting device according to claim 5, including means in slidable contact with said damping body in a liquid-tight manner for isolating said air chamber from outside of said damping body and for varying the volume of said air chamber.

10. A blood pressure waveform correcting device, comprising:
   a pressure correcting mechanism having an air chamber and a resistance passage, one end of said resistance passage communicating with said air chamber and an opposite end communicating with a blood pressure measuring line, said resistance passage comprising a curved passage, a passage composed of straight passages connected to one another, or a passage composed of straight and curved passages connected to one another, and said pressure correcting mechanism being defined by a body positioned in a housing, said air chamber and said resistance passage being formed as a part of said body, said air chamber being airtight, and including a plug held in slidable contact with said body in a liquid tight manner to isolate said air chamber from outside of said body and vary the volume of said air chamber, whereby a fluid in the blood pressure measuring line can flow through said resistance passage into said airtight chamber to directly dampen an extraneous pressure wave transmitted through the blood pressure measuring line.

11. A blood pressure waveform correcting device comprising:

a pressure correcting mechanism having an air chamber and a resistance passage that are formed as part of one-piece damping body, said air chamber having an opening that opens to one side of the damping body and said resistance passage also opening to said one side of the damping body, said air chamber being completely enclosed by said one-piece damping body except for the opening, and said one side of said damping body being in intimate contact with a wall member which has a hole passing therethrough, said hole in the wall member communicating with a blood pressure measuring line, one end of said resistance passage communicating with said hole in the wall member and the other end of said resistance passage communicating with said opening in the air chamber, said wall member including means in slidable contact with said damping body in a liquid-tight manner for isolating said air chamber from outside of said damping body and for varying the volume of said air chamber, whereby a fluid in the blood pressure measuring line can flow through said hole in the wall member, through the resistance passage and into the air chamber to dampen an extraneous pressure wave transmitted through the blood pressure measuring line.

12. The blood pressure waveform correcting device according to claim 11, wherein said airtight chamber has a volume ranging from about 1 $\mu$l to about 150 $\mu$l and said resistance passage has a cross-sectional area ranging from about 2000 $\mu m^2$ to about 160,000 $\mu m^2$ and a length ranging from about 0.5 mm to about 40 mm.

13. The blood pressure waveform correcting device according to claim 11, wherein said wall member includes means for permitting the wall member to be penetrated by a syringe needle.

14. The blood pressure waveform correcting device according to claim 11, wherein at least a portion of said wall member is made of a material capable of closing, of its own accord, a hole which has been pierced by a syringe needle.

* * * * *